(12) United States Patent
Hu et al.

(10) Patent No.: US 8,027,429 B2
(45) Date of Patent: Sep. 27, 2011

(54) DEVICE AND METHOD FOR REAL-TIME MARK OF SUBSTANCE IDENTIFICATION SYSTEM

(75) Inventors: Haifeng Hu, Beijing (CN); Kejun Kang, Beijing (CN); Li Zhang, Beijing (CN); Xuewu Wang, Beijing (CN); Qingping Huang, Beijing (CN); Yuanjing Li, Beijing (CN); Yinong Liu, Beijing (CN); Ziran Zhao, Beijing (CN); Zhen Wu, Beijing (CN)

(73) Assignees: Tsinghua University, Haidian District, Beijing (CN); Nuctech Company Limited, Haidian District, Beijing (CN)

( * ) Notice: Subject to any disclaimer, the term of this patent is extended or adjusted under 35 U.S.C. 154(b) by 66 days.

(21) Appl. No.: 12/492,739

(22) Filed: Jun. 26, 2009

(65) Prior Publication Data
US 2009/0323894 A1 Dec. 31, 2009

(30) Foreign Application Priority Data
Jun. 27, 2008 (CN) .......................... 2008 1 0115788

(51) Int. Cl.
*G01N 23/06* (2006.01)
*G01N 23/087* (2006.01)
*G01D 18/00* (2006.01)

(52) U.S. Cl. ............ 378/53; 378/56; 378/98.9; 378/207

(58) Field of Classification Search .................... 378/51, 378/53, 54, 56, 57, 62, 91, 98.9, 98.11, 98.12, 378/207, 210
See application file for complete search history.

(56) References Cited

U.S. PATENT DOCUMENTS

| | | | | |
|---|---|---|---|---|
| 5,319,547 A * | 6/1994 | Krug et al. | ...................... | 705/13 |
| 5,974,111 A * | 10/1999 | Krug et al. | ...................... | 378/57 |
| 6,597,759 B2 * | 7/2003 | Mazess et al. | .................. | 378/53 |
| 2006/0098733 A1 * | 5/2006 | Matsumura et al. | ...... | 375/240.03 |
| 2006/0140340 A1 * | 6/2006 | Kravis | ............... | 378/57 |
| 2007/0025505 A1 * | 2/2007 | Bjorkholm | ....................... | 378/53 |
| 2007/0183568 A1 * | 8/2007 | Kang et al. | ....................... | 378/57 |
| 2007/0286329 A1 * | 12/2007 | Wang et al. | ....................... | 378/2 |
| 2009/0129544 A1 * | 5/2009 | Chen et al. | ....................... | 378/62 |
| 2009/0310744 A1 * | 12/2009 | Petch et al. | ....................... | 378/53 |

* cited by examiner

*Primary Examiner* — Anastasia Midkiff
(74) *Attorney, Agent, or Firm* — Osha • Liang LLP (57) ABSTRACT

Disclosed are a method and a device for real-time mark for a high-energy X-ray dual-energy imaging container inspection system in the radiation imaging field. The method comprises the steps of emitting a first main beam of rays and a first auxiliary beam of rays having a first energy, and a second main beam of rays and a second auxiliary beam of rays having a second energy; causing the first and second main beams of rays transmitting through the article to be inspected; causing the first and second auxiliary beams of rays transmitting through at least one real-time mark material block; collecting values of the first and second main beams of rays that have transmitted through the article to be inspected as dual-energy data; collecting values of the first and second auxiliary beams of rays that have transmitted through the real-time mark material block as adjustment parameters; adjusting the set of classification parameters based on the adjustment parameters; and identifying the substance according to the dual-energy data based on adjusted classification parameters. The method according to the invention simplifies the mark procedure for a substance identification subsystem in a high-energy dual-energy system while improves the stability of the material differentiation result of the system.

23 Claims, 10 Drawing Sheets

FIRST OF ALL, alphaL AND alphaH ARE DEFINED AS FOLLOWS:

alphaL = (1-log(TL))*1000, WHEREIN TL IS THE LOW-ENERGY TRANSPARENCY;

alphaH = (1-log(TH))*1000, WHEREIN TH IS THE HIGH-ENERGY TRANSPARENCY.

THE alphaH IS CONSIDERED AS THE ABSCISSA alphaX OF THE alpha CURVE,

AND THE DIFFERENCE OF alphaL AND alphaH IS CONSIDERED AS THE ORDINATE alphaY OF THE alpha CURVE:

alphaX = alphaH = (1-log(TH))*1000;

alphaY = alphaL - alphaH = (-log(TL)+log(TH))*1000

DEVICE AND METHOD FOR REAL-TIME MARK OF SUBSTANCE IDENTIFICATION SYSTEM

FIELD OF THE INVENTION

The present invention is related to a field of radiation imaging, and particularly, to a device and method of real-time mark of a substance identification system that is capable of simplifying the mark procedure of the substance identification system and improving the stability of the substance identification result of the system.

BACKGROUND OF THE INVENTION

It is a modern and advanced transportation mode to take a container as a unit for transportation. Containerization has become the main trend of the international cargo transportation. Meanwhile, the uses of containers in smuggling firearms, weapons, drugs, explosives, even WMDs (Weapons of Mass Destruction) and RDDs (Radiological Dispersal Devices) have become an international public hazard troubling every government and interfering with the normal order of the international cargo transportation.

Since 9.11 in U.S., the U.S. government began to attach great importance to the potential risks of the cargo transportation, and worried more about WMDs and RDDs through containers into the United States. To guard against such risks, the U.S. Customs Office issued a "Container Security Initiative (CSI)" in Jan. 17, 2001, in which all the foreign ports with transactions directly linked to the U.S. port were required to be equipped with non-invasive $X(\gamma)$-ray scanning imaging equipments for performing ray-scanning inspections on the containers shipped to the U.S. One year after CSI being announced, there were 18 major ports in the world which joined the initiative and began to operate. In the background where the requirements for the international transportation safety are increasing, the World Customs Organization unanimously adopted a resolution calling for all the 161 members to develop a plan regarding the container security inspection along the mode of the CSI, i.e the container security inspection has become a world's common topic of concern.

The existing container $X(\gamma)$-ray security inspection equipments mainly aim at transmission imaging, i.e. to directly penetrate cargo using X-rays so as to obtain transmission images of all the articles covered by the path of the X-rays. The standard transmission imaging technology solves the "visualization" problem of containers, such that it has been widely used. A dual-energy transmission technique is developed from the transmission imaging technology. In the dual-energy transmission technique, X-rays having two different energy spectra transmit the inspected article. The acquired differences between the signals of the X-rays are processes to obtain atomic number information of a material in an article being inspected. This technology can effectively improve effect of security inspection to a certain extent, and the requirements proposed by CSI for the trend from inspection for smuggling to inspection for dangerous articles can be met. A substance identification system adopting this technique has been successfully implemented in a high-energy X-ray dual-energy imaging container inspection system, with advantages of high operating speed, accurate identification and so on.

The substance identification subsystem in the high-energy-X-ray dual-energy imaging container inspection system (referred to as "high-energy dual-energy system" below for short), however, has the following disadvantages.

An individual mark procedure is necessary to obtain a set of classification parameters suitable for a system before usage because the dual-energy state of each system is different from another. The marking is one of the most complicated processes during testing a dual-energy system.

Furthermore, the dual-energy state will fluctuate in an accelerator subsystem in a high-energy dual-energy system for various reasons such as a long haul, exchange of elements, a dose adjustment by human operator, and so on. Re-mark is needed when the fluctuation is significant.

Moreover, the dual-energy state of the accelerator such as pulse current fluctuation and state fluctuation due to AFC will vary over time even for the same accelerator, which is caused by the limitation of the accelerator technique. Due to the varying of the state, identification results will be different at different times for the same substance, resulting in a degraded image quality.

SUMMARY OF THE INVENTION

An object of the invention is to provide a device and method of real-time mark for a substance identification system, such as a high-energy dual-energy system, that is capable of simplifying the mark procedure of the system and improving the stability of the substance identification result of the system.

The invention aims at overcoming the disadvantages in the existing substance identification system, for example, the high-energy dual-energy system. A device according to the invention not only makes it possible for systems with energy and dose being slightly different from each other use a set of classification parameters, but also can remove the requirement for re-mark of an accelerator subsystem of a system after state change thereof. Furthermore, a device according to the invention can improve the material identification result which may be affected by fluctuation over time of the dual-energy state of the accelerator.

In accordance with first aspect of the invention, it provides a real-time mark method for a substance identification system which identifies a substance in an article to be inspected based on a set of classification parameters. The method comprises the steps of: emitting a first main beam of rays and a first auxiliary beam of rays having a first energy, and a second main beam of rays and a second auxiliary beam of rays having a second energy; causing the first and second main beams of rays transmitting through the article to be inspected; causing the first and second auxiliary beams of rays transmitting through at least one real-time mark material block; collecting values of the first and second main beams of rays that have transmitted through the article to be inspected as dual-energy data; collecting values of the first and second auxiliary beams of rays that have transmitted through the real-time mark material block as adjustment parameters; adjusting the set of classification parameters based on the adjustment parameters; and identifying the substance according to the dual-energy data based on adjusted classification parameters.

According to an embodiment of the invention, adjusting the set of classification parameters based on the adjustment parameters is performed every predetermined times of scanning.

According to an embodiment of the invention, the at least one real-time mark material block comprises a first block representing an organic substance, a second block representing a mixture, a third block representing an inorganic substance and a fourth block representing a heavy metal.

According to an embodiment of the invention, the first block is made of carbon, the second block is made of aluminum, the third block is made of iron and the fourth block is made of lead.

According to an embodiment of the invention, the real-time mark method further comprises a step of adjusting energy spectrum of respective beams of rays by an energy spectrum adjustment unit.

According to an embodiment of the invention, the first auxiliary beam of rays is part of the first main beam of rays, and the second auxiliary beam of rays is part of the second main beam of rays.

According to an embodiment of the invention, the first auxiliary beam of rays is separated from the first main beam of rays, and the second auxiliary beam of rays is separated from the second main beam of rays.

According to an embodiment of the invention, the at least one real-time mark material block is arranged in the upper portion, lower portion or side portion of the first or second main beam of rays.

According to an embodiment of the invention, the at least one real-time mark material block has a single thickness respectively.

According to an embodiment of the invention, the at least one real-time mark material block has at least two thicknesses respectively.

According to an embodiment of the invention, the classification parameters form a discretized classification curve that can differentiate at least two substances from each other.

In accordance with another aspect of the invention, it provides a real-time mark device for a substance identification system which identifies a substance in an article to be inspected based on a set of classification parameters. The real-time mark device comprises a ray generation unit for emitting a first main beam of rays and a first auxiliary beam of rays having a first energy, and a second main beam of rays and a second auxiliary beam of rays having a second energy, the first and second main beams of rays transmitting the article to be inspected, the first and second auxiliary beams of rays transmitting through at least one real-time mark material block; a collection unit for collecting values of the first and second main beams of rays that transmit through the article to be inspected as dual-energy data, and collecting values of the first and second auxiliary beams of rays that transmit through the real-time mark material block as adjustment parameters; a data processing unit for adjusting the set of classification parameters based on the adjustment parameters, and identifying the substance according to the dual-energy data based on adjusted classification parameters.

According to an embodiment of the invention, the collection unit further comprises a main detector module, whose detection surface being substantially perpendicular to a center line of the first or second main beam of rays, and for detecting the first or second main beam of rays that has transmitted through the article to be inspected; an auxiliary detector module, whose detection surface being substantially perpendicular to a center line of the first or second auxiliary beam of rays, and for detecting the first or second auxiliary beam of rays that has transmitted through the real-time mark material block.

The device according to the invention can be incorporated in the substance identification subsystem of a high-energy dual-energy system. For a high-energy dual-energy system with high substance identification accuracy, a set of classification parameters applicable for the system and calibrated in advance is adjusted in real time by means of a device according to the invention, to make it usable. Consequently, there is no need for a dual-energy system to be calibrated individually before usage, resulting in a hardware cost lowered for the auto mark device and a reduced time for system adjustment. For a high-energy dual-energy system with low substance identification accuracy, it is better to perform mark before usage in order to achieve an optimal material differentiation effect. When the dual-energy state of the accelerator of the system changes, the original classification parameters are adjusted in real time by means of a real-time mark device according to the invention to make them usable. Thereby re-mark is unnecessary, and maintenance time is reduced.

BRIEF DESCRIPTION OF THE DRAWINGS

The features and advantages of the invention can be apparent from the following detailed descriptions with reference to the accompanying drawings, wherein.

DETAILED DESCRIPTION OF THE PREFERRED EMBODIMENTS

The preferred embodiment of the invention will now be described more fully hereinafter with reference to the accompanying drawings. In the drawings the same reference numerals are used for denoting the same or similar components that are shown in different figures.

The method and device according to an embodiment of the invention are based on high-energy dual-energy data. For clarity, the rays having a high energy in the high-energy X-ray dual-energy system are referred to as high-energy X-rays, and those having a low energy are referred to as low-energy X-rays. The method and device according to an embodiment of the invention are applicable for a high-energy dual-energy system in the energy range of 3 MeV-10 MeV.

Figure 1:
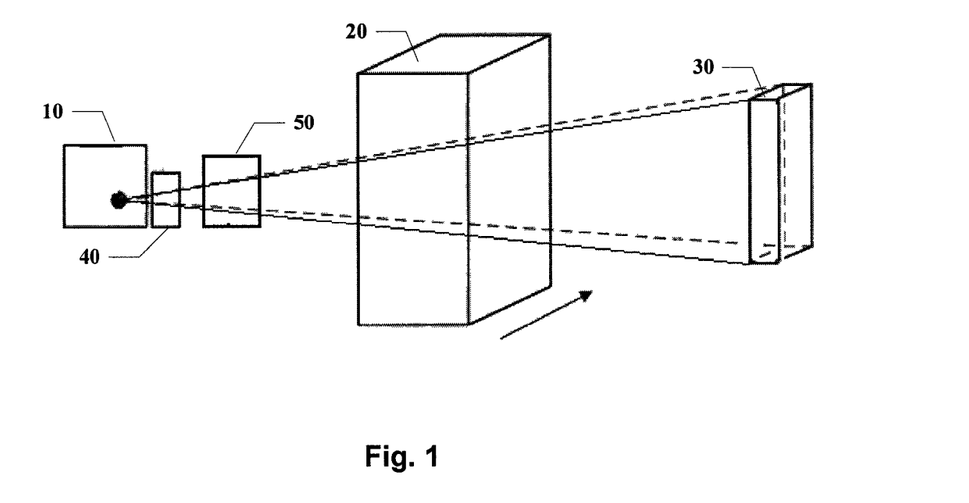
FIG. 1 is a schematic diagram of a high-energy dual-energy system.

FIG. 1 is a schematic diagram of a high-energy dual-energy system. As shown in FIG. 1, the high-energy dual-energy system comprises a ray generation unit 10, a energy spectrum shaping unit 40, an auto mark unit 50, a mechanical transmission unit (not shown), a data collection subsystem 30, a scanning controlling and data processing computer (not shown). The ray generation unit 10, the mechanical transmission unit, the data collection subsystem 30 and the scanning controlling and data processing computer are basic components of a high-energy X-ray dual-energy imaging container inspection system, whereas the energy spectrum shaping unit 40 and the auto mark unit 50 belong to a substance identification subsystem. The real-time mark device according to an embodiment of the invention is also a part of the substance identification subsystem.

According to an embodiment of the invention, the ray generation unit 10 is provided with a dual-energy X-ray accelerator and corresponding auxiliary devices. The ray generation unit 10 generates beams of X-rays having two different energy levels alternately in a high frequency, such as a first beam of rays having 3 MeV and a second beam of rays having 8 MeV. The center line of the beams of rays is substantially perpendicular to a detection plane of a detector module in the data collection subsystem.

The energy spectrum shaping unit 40 is provided with an energy spectrum shaping material and corresponding auxiliary device. The energy spectrum shaping unit 40 is arranged between the ray generation unit 10 and the article 20 to be inspected in order to shape the energy spectrum of rays that are outputted from the ray generation unit 10, such as an accelerator, before the rays transmit the article 20 to be inspected, so that the spectrum distribution is favorable for material differentiation.

Figure 4:
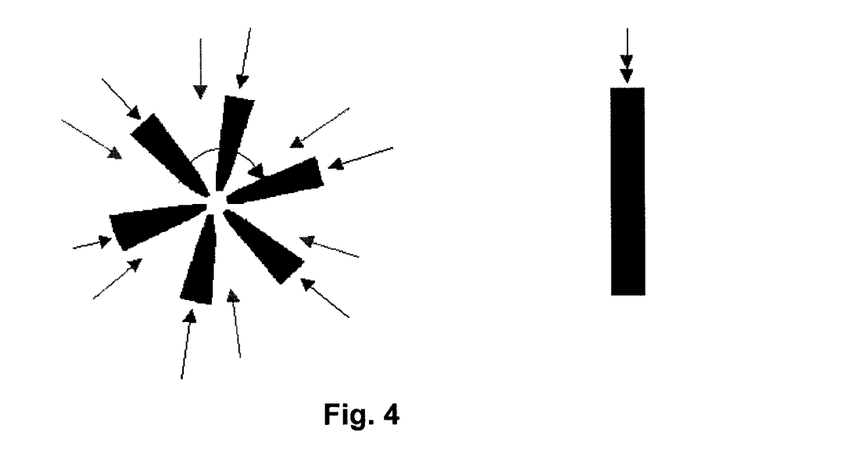
FIG. 4 is a schematic diagram of an energy spectrum shaping unit according to an embodiment of the invention, wherein the black arrow denotes rays having a high energy, the gray arrow denotes rays having a low energy, and the black area denotes a material block being shaped.

As shown in FIG. 4, characteristic of an energy spectrum shaping material consists in large attenuation to low-energy rays while low attenuation to high-energy rays. The better the characteristic is, the better the result of energy spectrum shaping is. Any material that meets this characteristic can be used as the energy spectrum shaping material. For such characteristic of the energy spectrum shaping material, the equivalent energy of rays increases after the energy spectrum shaping. If the shaping material only acts on the high-energy rays, the equivalent energy of the high-energy rays increases while that of the low-energy rays maintains, thereby the energy difference between the two energies is enlarged so as to improve the material differentiation capability of the system.

Based on such characteristic, the carbon is used as the shaping material. In principle, the thicker the shaping material is, the better the material differentiation is. However, taking statistical fluctuation into consideration, the thicker the shaping material is, the fewer doses the detector receives, and thus the lower the SNR of data is. Accordingly, there is an optimal for the thickness of the shaping material, which depends on the specific case of the system. According to energy distribution of rays of a high energy and a low energy, it is determined that only rays having certain energy are subject to energy spectrum shaping. FIG. 4 shows, in the left side, a schematic diagram of an energy spectrum shaping unit in a turntable form. Alternatively, rays of two energies are subject to energy spectrum shaping. FIG. 4 shows, in the right side, an energy spectrum shaping unit that can perform energy spectrum shaping on rays having two energies.

The design of the energy spectrum shaping unit 40 depends on the requirement of energy spectrum shaping. It is possible to only perform energy spectrum shaping on high-energy rays. In this case, the energy difference between the two energies is enlarged due to increasing of equivalent energy of high-energy rays, whereby the material differentiation capability of the system is improved. Specially, it is also possible to perform energy spectrum shaping on rays having both energies, especially for the case that the low energy is about 3 MeV. From the mass attenuation coefficient curve shown in FIG. 3, it can be seen that the attenuation coefficients of low-Z materials approximate and the slopes thereof are all small in the region around 3 MeV energy. Therefore, in this region, change of energy has little impact on the differentiation capability of a low-Z material. However, the attenuation coefficient of a high-Z material forms an inflexion near 3 MeV. As a result, the lead can not be differentiated from other materials under this energy. Consequently, low-energy rays, i.e. rays having an energy of 3 MeV, are performed energy spectrum shaping, the low-energy part in the rays of a low energy is absorbed by the energy spectrum shaping material, so that the differentiation capability of a high-Z material is improved while no negative impact on a low-Z material is introduced.

Figure 5:
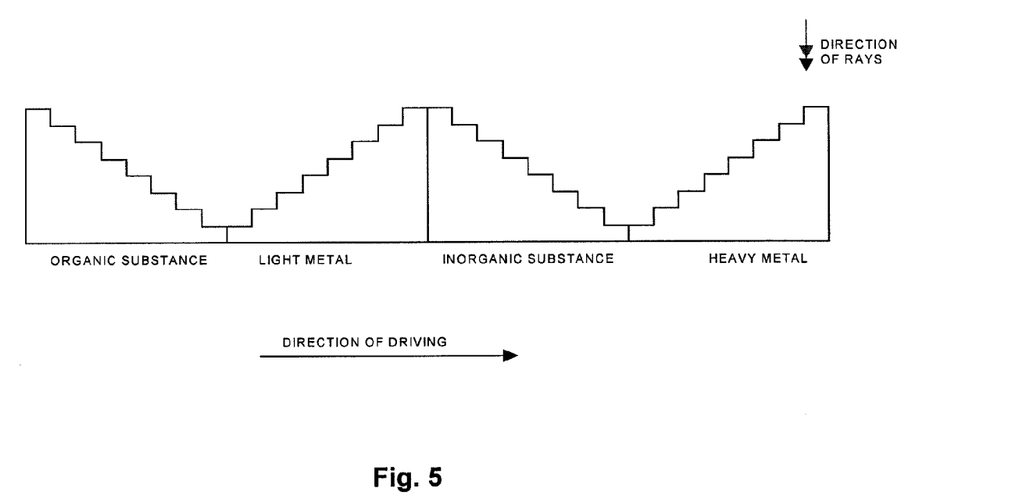
FIG. 5 is a schematic diagram of an auto mark unit according to an embodiment of the invention, wherein the black arrow denotes rays having a high energy and the gray arrow denotes rays having a low energy.

As shown in FIG. 5, the auto mark unit 50 includes a mark material in a shape of a step and corresponding auxiliary device. The auto mark unit is adapted to collect mark data, acquire in real time classification parameters corresponding to state of the system through processing of an auto mark module in a computer, as input to an auto identification module.

Here, the mark materials comprise various typical materials. To ensure mark accuracy, at least one type of typical material may be prepared per category. Alternatively, several types of typical materials with difference equivalent atomic numbers may be prepared per category. If there is no material prepared, or there is a limited space for placing the automatic mark device 50, the materials of middle categories may be omitted, and the automatic mark algorithm may use an interpolated value of data of the adjacent category instead. The selection of the mark materials may be associated with the material discrimination requirements for the system. The requirements for the high-energy X-ray dual-energy may be divided into four categories, i.e. organic substance, light metals, inorganic substance and heavy metals. Therefore, four types of typical materials are selected from the above four categories, i.e. graphite ($Z=6$), aluminum ($Z=13$), iron ($Z=26$) and lead ($Z=82$) in turn. The selection of these four types of materials is based on two reasons. One is these materials are commonly used, and the other is each of them belongs to an elementary substance, which is of stable nature.

For each material, several classes of steps should be designed from thin to thick. The thinnest thickness and the thickest thickness depend on the material discrimination range of the system. The number of the classes of the steps may be decided by the mark accuracy in together with the space for placing the automatic mark device.

The auxiliary devices mainly provide the mechanical driving and realize the localization scanning so as to obtain dual-energy transmission data of each step for each material. When several columns of dual-energy transmission data are required at each localization point, more than 256 columns are recommended to scan, thereby largely eliminating the effect of the signal statistical fluctuation.

In the direction of the height, the angular distributions for the X-rays, received by the different detectors, over the arm supports of the detectors are different. The spectrum distributions for different angular distributions are different, thereby leading to different parameters for the material discrimination. Therefore, taking the effect of the angular distributions of the X-rays into account, all of the detecting heights may be divided into several regions, each having an independent statistic, so as to generate a classification parameter. This requires that the mark materials in the automatic mark device 50 should cover all the spans of interest.

If the heights of the mark materials are limited by objective factors, such as the processing capacity, the equipment space, and so on. It is impossible to cover all the detector modules on the art support. A simplified manner is as follows. Under normal circumstances, the most interested detecting height is located in a position where the container places cargo, and the system usually adjusts the main beam of the X-ray to the vicinity of that position. As a result, the main beam of the rays is focused on the important mark object. The mark materials may be designed to only cover the region. Then the obtained dual-energy transmission data is inputted into the automatic mark algorithm as its parameter, to generate a classification parameter corresponding to the energy spectrum distribution in the main beam direction of the X-ray, as a classification parameter for all of the detecting regions. This simplified manner lies within the allowance error range, with the angular distribution of the X-ray being smaller.

Figure 3:
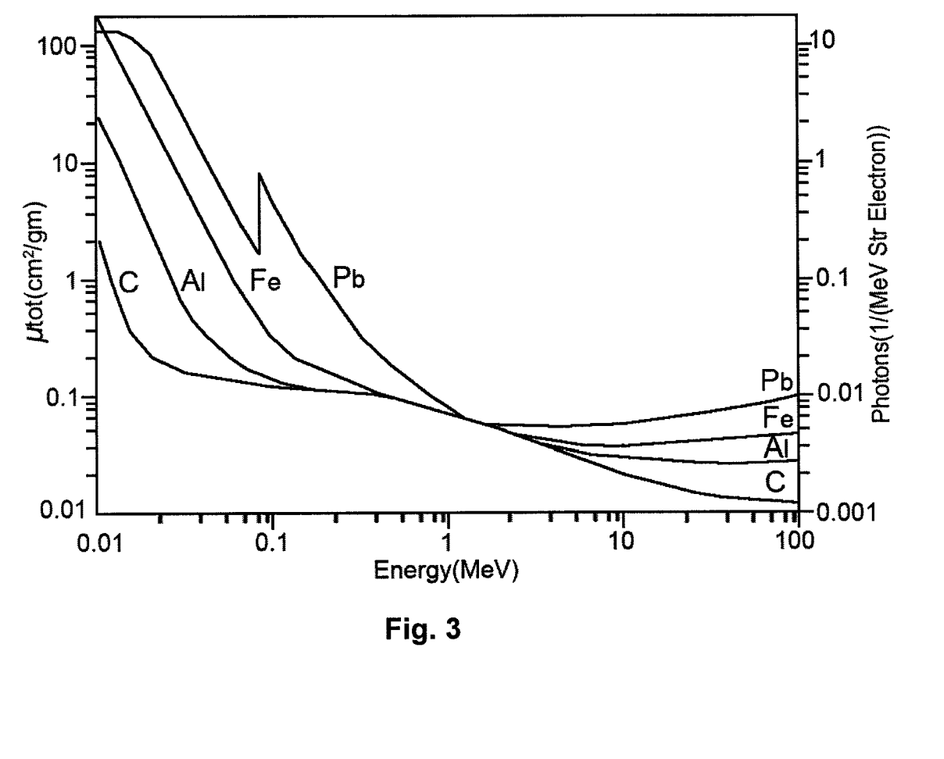
FIG. 3 shows a mass attenuation coefficient curve.

The mark materials in the automatic mark device 50 may be designed to be in any forms as long as the above requirements are met. In FIG. 3, the order number of the steps and the thickness of the steps are described only for illustration, without indicating any actual meanings.

The mechanical transmission unit has the ray generation unit 10 and the data collection subsystem 30 move together with respect to the article to be inspected in the horizontal direction. It is possible that the ray generation unit 10 and the data collection subsystem 30 do not move while the article to be inspected moves. It is also possible that the ray generation unit 10 and the data collection subsystem 30 move while the article to be inspected does not move.

The data collection subsystem 30 mainly includes a linear detector for detecting the dual-energy X-rays generated by the ray generation unit 10 after they have transmitted the article 20 to be inspected, generating dual-energy transmission data and sending it to the scanning controlling and data processing computer. The data collection subsystem 30 further includes a circuit and logic control unit for sensing projection data from the detector, etc. The detector may be a solid detector, a gas detector or a semiconductor detector.

The scanning controlling and data processing computer is responsible for main controlling for the operation of the inspection system, including mechanical controlling, electrical controlling, security controlling, and so on. The scanning controlling and data processing computer is further responsible for processing and displaying of dual-energy transmission data collected by the data collection subsystem.

Figure 2:
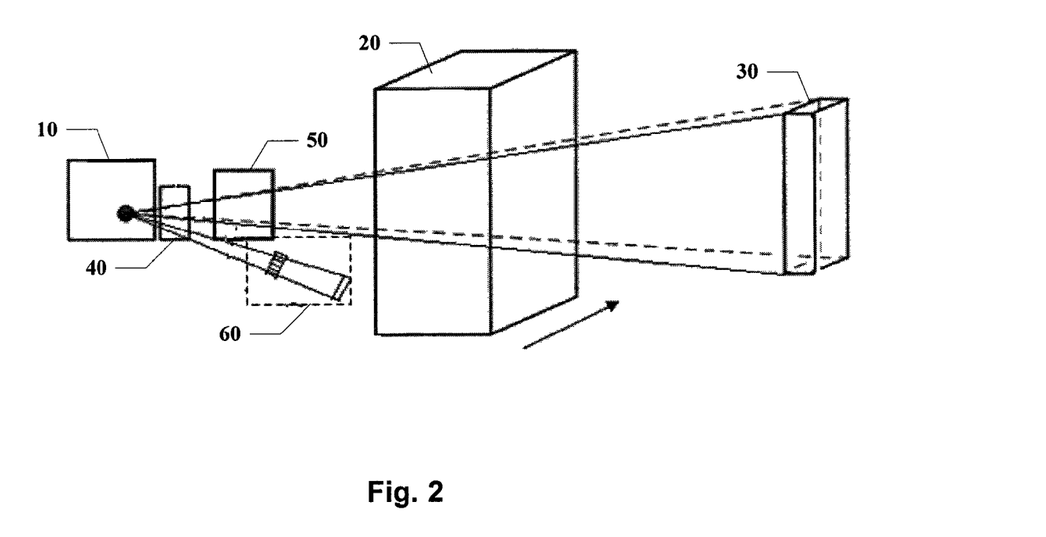
FIG. 2 is a schematic diagram of a high-energy dual-energy system incorporated therein a real-time mark device, sizes of each part being illustrative and having no actual meaning.

A real-time mark device 60 is introduced to perform real-time mark on classification parameters so as to simplify the mark procedures of the substance identification system and improve material differentiation result. FIG. 2 is a schematic diagram of a substance identification system with the real-time mark device 60 being incorporated therein.

Figure 6:
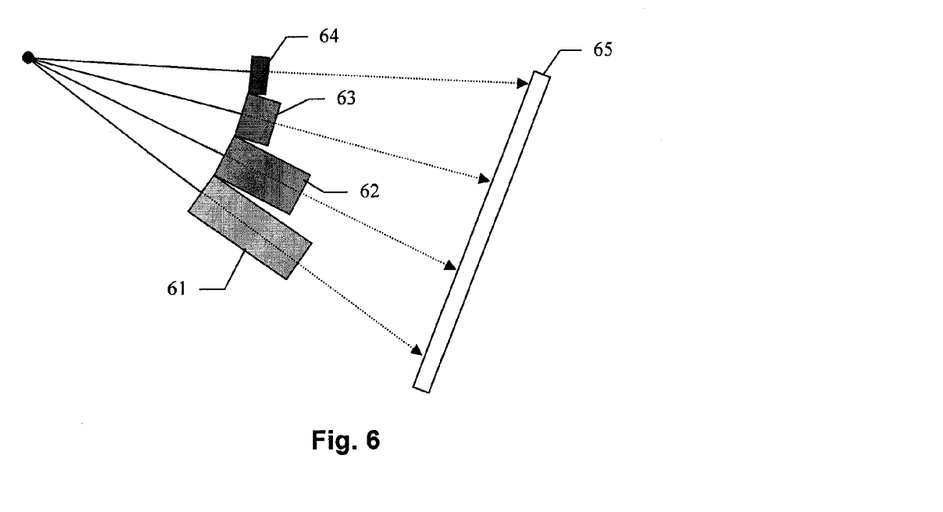
FIG. 6 is a schematic diagram of a real-time mark device.

As shown in FIG. 6, the real-time mark device 60 includes real-time mark materials 61~64, a real-time mark detection module 65 and auxiliary device (not shown).

The real-time mark device 60 should be so arranged that it is coverable by rays while it will not block beams of rays to the object to be inspected.

According to an embodiment of the invention, the real-time mark device should be arranged adjacent the accelerator. Depending on models of the high-energy dual-energy system, the real-time mark device can be arranged in the upper portion, lower portion or side portion of sectorial beams of rays required by a normal scanning.

In this way, the ray generation unit 10 which needs, for example, a beam being arranged on the upper portion, lower portion or side portion of sectorial beams of rays required by a normal scanning to supplement auxiliary beams of rays.

Furthermore, according to an embodiment of the invention, the real-time mark material block usually includes four kinds of materials, i.e. an organic material, a mixture, an inorganic material and a heavy metal with thicknesses thereof depending on the real system. An organic material block 61, a mixture block 62, an inorganic material block 63 and a heavy metal block 64 are shown in FIG. 6. In the high-energy dual-energy system, usually carbon, aluminum, iron and lead are selected from the four kinds of materials as typical materials. Only one ~ three kinds of materials from carbon, aluminum, iron and lead can be adopted and information about other materials is obtained by weighting of the information of the adopted materials if the classification requirement on a kind of material is low or the space is too small. The real-time mark material block is required to cooperate with an auto control unit which controls shifting of the real-time mark material block in the horizontal direction. The purpose for the auto control unit is to move the real-time mark material block off when the system collects air and background, so as to prevent it from blocking the auxiliary beams of rays.

The real-time mark detection module 65 collects information of the attenuated rays for all materials in the real-time mark material block. The real-time mark detection module 65 is such arranged that the detection plane (surface) thereof is perpendicular to the center line of the auxiliary beams of rays. Data collected by the detection module 65 (referred to as auxiliary image below) is combined with data from the data collection subsystem 30, and transmitted therefrom to the data processing computer for real-time adjustment of classification parameters available for image data classification.

According to an embodiment of the invention, the design for coverage angle of auxiliary beams of rays, height of real-time mark material block and the number of units in the real-time mark detection module should be considered collectively. The design principle is that data for each material contains several pixels on the collected auxiliary image. Preferably the effective pixels of each material are not less than 6 pixels, so as to reduce statistical fluctuation in the statistical procedure.

Figure 7:
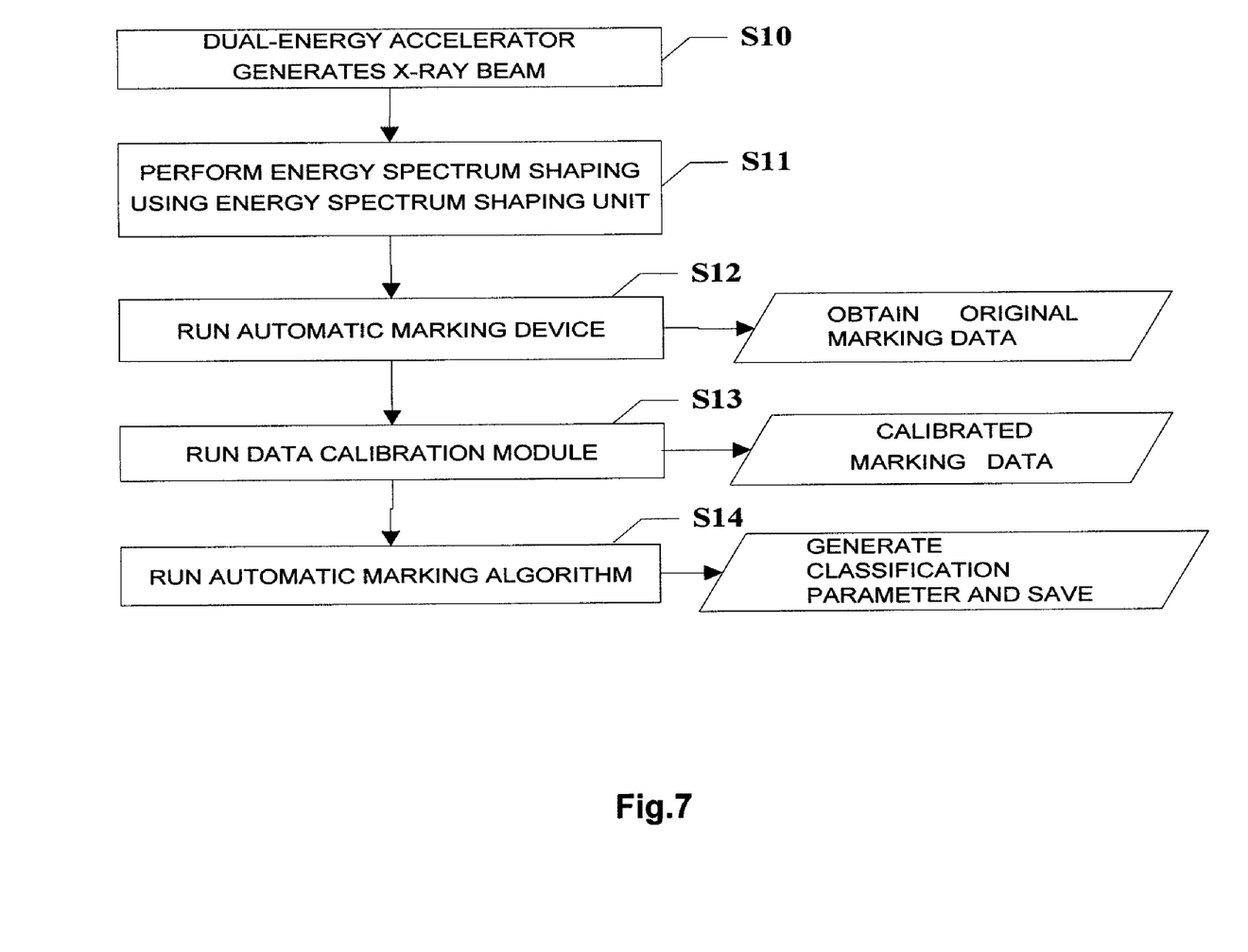
FIG. 7 is a flowchart showing an auto mark procedure according to an embodiment of the invention.

FIG. 7 is a flowchart showing an auto mark procedure according to an embodiment of the invention. The auto mark unit 50 is triggered manually after the substance identification system has been installed, to acquire original mark data and classification parameters of the system.

As shown in FIG. 7, the ray generation unit 10 generates beams of X-rays at step S10. At step S11, the beams of X-rays are shaped by the energy spectrum shaping unit 40 to obtain beams of X-rays that are favorable for material differentiation. An auto mark processing is to be performed at step S12, where an auto mark procedure is triggered manually and conducted to acquire in real time original mark data.

Next, at step S13, data calibration processing is performed on the original mark data to eliminate impact brought by detector base, detector uniformity and ray dose fluctuation. At step S14, an auto mark algorithm is run to generate classification parameters and store them in files.

As described above, each time the system state changes, the auto mark procedure is trigged manually to start the auto mark unit 50 which collects original mark data that has been subject to energy spectrum shaping and transmits it from the data collection subsystem to the data processing computer. The material differentiation algorithm is designed by using an alpha curve. Accordingly, the auto mark algorithm is to compute classification parameters of an alpha curve that corresponds to the system state. Classification parameters of an alpha curve that corresponds to the system state are obtained by invoking the auto mark algorithm, and stored in a file as parameters inputted to the material differentiation block. The coordinate definition for the alpha curve is shown in FIG. 9.

Figure 9:
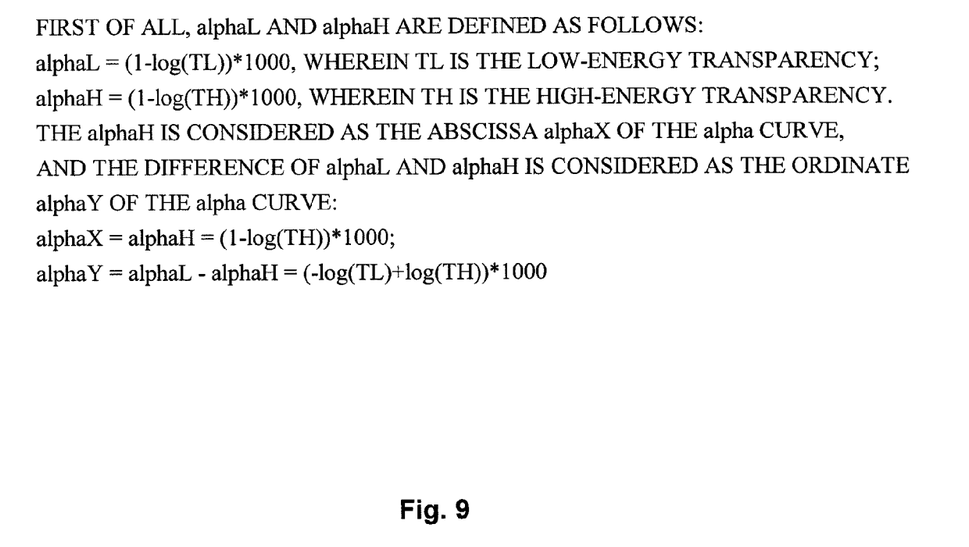
FIG. 9 shows coordinate definition for an alpha curve.

As shown in FIG. 9, alphaL and alphaH are defined as follows.

alphaL=(1−log(TL))*1000, wherein TL is the low-energy transparency;

alphaH=(1−log(TH))*1000, wherein TH is the high-energy transparency.

The alphaH is considered as the abscissa alphax of the alpha curve, and the difference of alphaL and alphaH is considered as the ordinate alphay of the alpha curve:

alphax=alphaH=(1−log(TH))*1000;

alphay=alphaL−alphaH=(−log(TL)+log(TH))*1000.

Figure 10A:
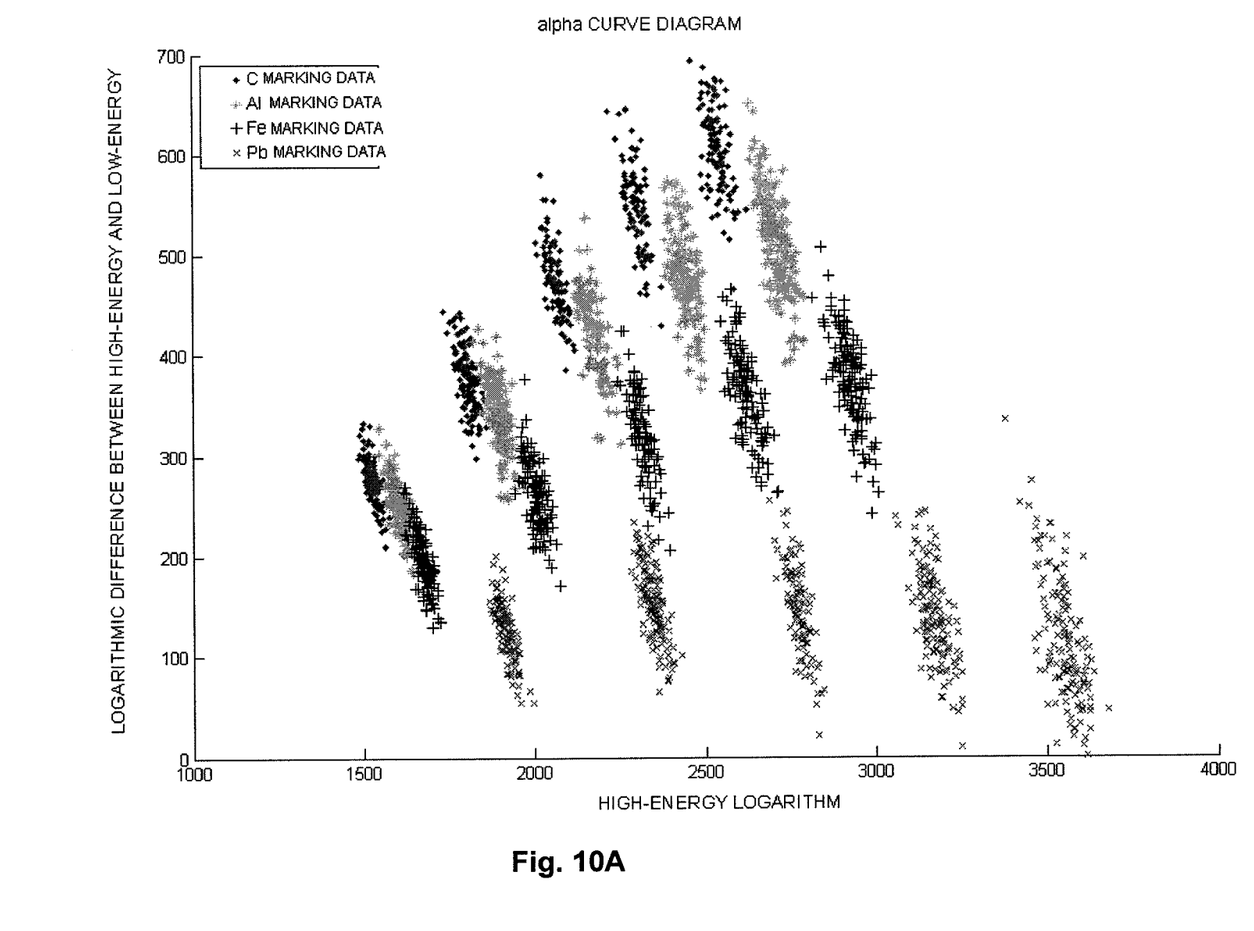
FIG. 10A is a schematic diagram showing training data for a mark material used in an auto mark procedure.

As described above, in step S13, a data calibration module is invoked to calibrate the original mark data, so as to eliminate impact brought by detector background, detector non-uniformity and ray dose fluctuation, resulting in training data for the mark material. FIG. 10A is a schematic diagram of the training data within some detecting span in the alphas curve diagram.

A process for generating a classification boundary among various types of materials from the training data of the mark material will be described in a greater detail as follows.

(i) Within some detecting span, a mean value statistic is performed sequentially on several columns of calibrated dual-energy data of each step for each material, so as to obtain a series of mean value points for the training data of the mark material. FIG. 10C is a schematic diagram of the mean value points for the training data within some detecting span in the alpha curve diagram.

Figure 10B:
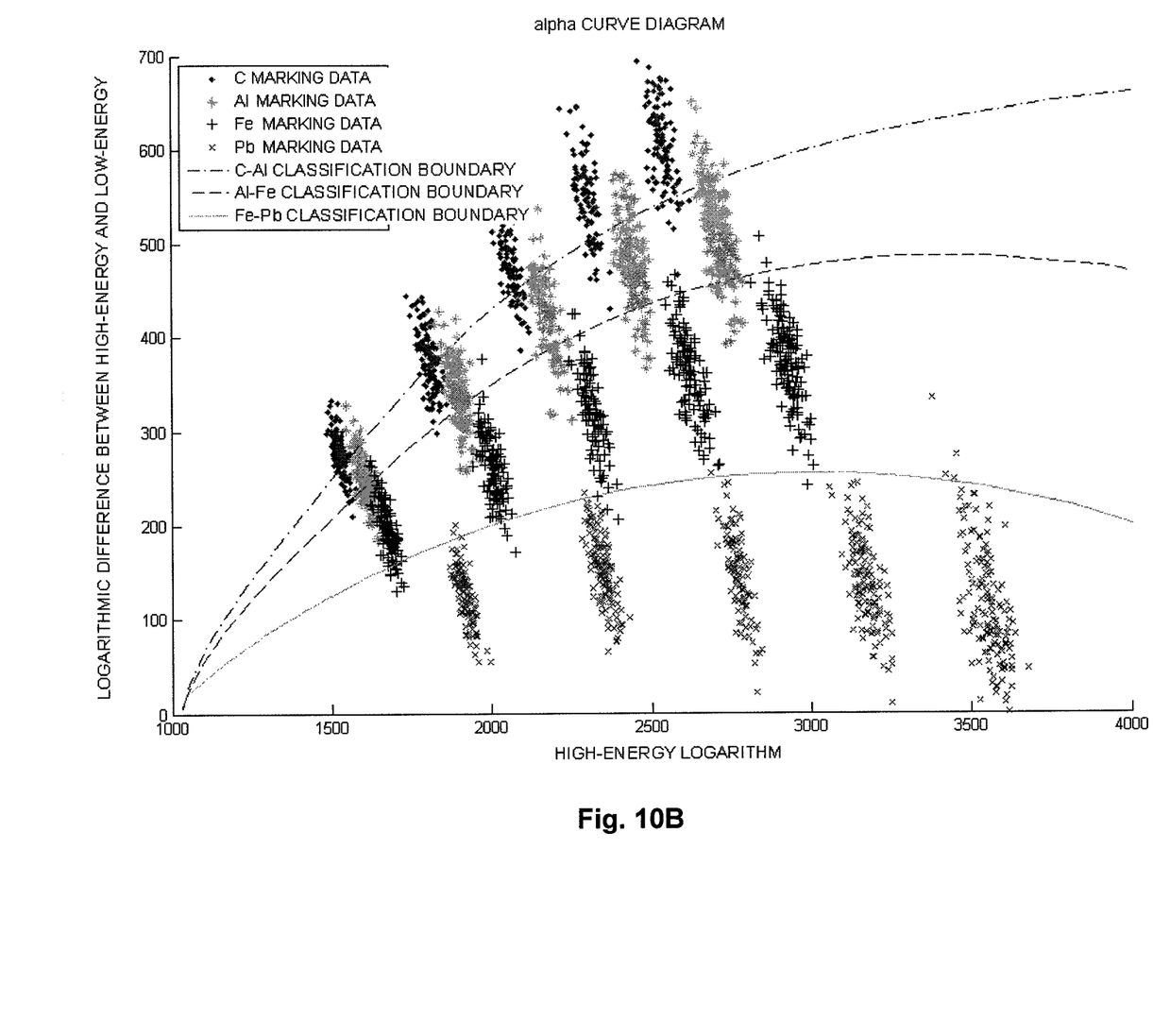
FIG. 10B is a schematic diagram showing an alpha curve generated from the training data for the mark material.
Figure 10C:
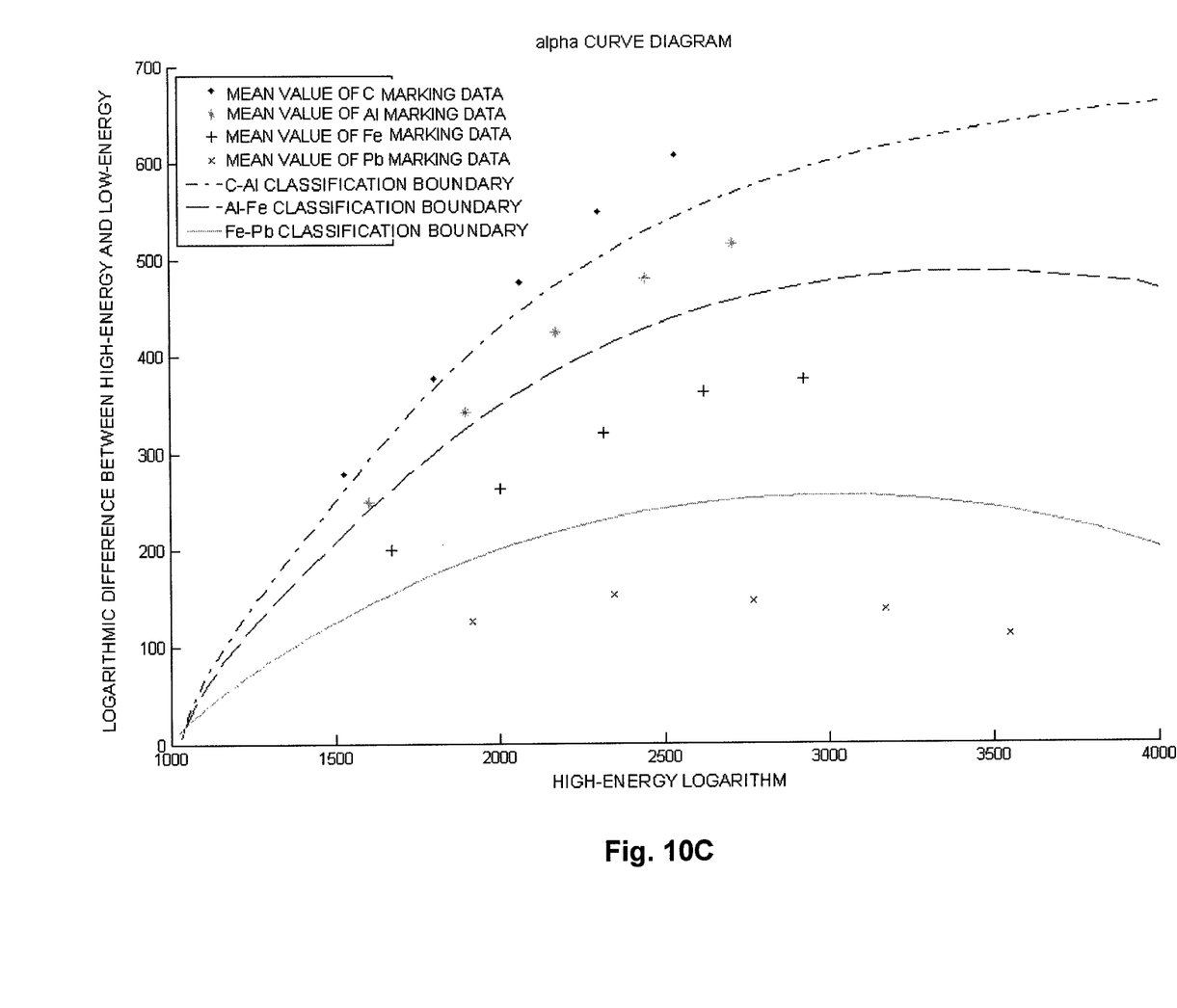
FIG. 10C is a statistical chart of the training data for the mark material.

(ii) In the alpha curve diagram of FIG. 10B, several mean value points for the training data of some type of material are connected in together, so that a discrete alpha curve for that material may be obtained. However, since the order number of the steps of the mark material is limited, the discrete alpha curve obtained directly from connecting is of quite low accuracy. Therefore, the least square curve fitting method can be adopted to perform curve fitting, i.e. to obtain a fitting polynomial of a given data point by means of the least square method. Several mean value points of the training data are considered as input parameters for the curve fitting such that a fitting parameter for the curve, i.e. the coefficients of respective orders of the polynomial, may be obtained. The order of the fitting polynomial is selected relying on the actual situation. The curve fitting may also adopt the other fitting methods, such as the optimum fitting polynomial under Chebyshev.

(iii) A discretization is performed on the x-axis of the alpha curve, the discrete accuracy for which depends on necessities. Then, y-axis data corresponding to each discrete point may be calculated by using the curve fitting parameters. Through this step, a discretization alpha curve for the material may be obtained.

(iv) Repeat steps (ii) and (iii) until the discretization alpha curves for all the materials may be obtained.

(v) From FIG. 10B, it can be seen that the alpha curve is monotonous along the direction of the atomic number, based on which the dual-energy material differentiation algorithm is. Therefore, a discrete boundary between two adjacent curves can be successively computed once discretized curves for respective materials are obtained, as shown in FIG. 10C.

The classification of the four types of categories depends on the equivalent atomic number: Z=1~10 is classified into a category of organic substance; Z=10~18 is classified into a category of light metals; Z=18~57 is classified into a category of inorganic substance; and Z>57 is classified as a category of heavy metals. Graphite (Z=6), aluminum (Z=13), iron (Z=26) and lead (Z=82) are selected for the four types of typical materials respectively. A discretization alpha curve for an atomic number of Z=10, i.e. a classification boundary between organic substance and inorganic substance, is obtained by performing weighted averaging on a discretization alpha curve for the material of graphite (Z=6) and a discretization alpha curve for the material of aluminum (Z=13). Among the other things, the weighted value of the weighted averaging may be simply calculated based on the atomic number, i.e. it is assumed that distinguishabilities within different ranges of the atomic number are the same. Although distinguishabilities within different ranges of the atomic number should be different by strictly speaking, since the high-energy dual-energy is different from the low-energy dual-energy in that the material discrimination ability thereof is relatively poor, only the materials belonging to different categories may be distinguished, while the materials with different atomic numbers can not be accurately distinguished. Therefore, such difference is acceptable.

Similarly, a discretization alpha curve for an atomic number of Z=18, i.e. a classification boundary between light metals and inorganic substance, is obtained by performing weighted averaging on a discretization alpha curve for the material of aluminum (Z=13) and a discretization alpha curve for the material of lead (Z=82). A discretization alpha curve for an atomic number of Z=57, i.e. a classification boundary between inorganic substance and heavy metals, is obtained by performing weighted averaging on a discretization alpha curve for the material of iron (Z=26) and a discretization alpha curve for the material of lead (Z=82).

(vi) Repeat steps (i), (ii), (iii), (iv) an (v) until discretization classification boundaries for all the detection spans are obtained.

Data for the classification boundaries of various types of typical materials, among various detecting spans, is saved in a file as a classification parameter for the material discrimination module.

As described above, the material discrimination is a distinguished feature for the dual-energy X-ray system from the single-energy X-ray system. Since the material discrimination ability obtained by the high-energy X-ray imaging is much worse than that of the low-energy dual-energy X-ray technology. Therefore, it is required for the material discrimination module to not only consider how to perform a classification correctly, but also consider how to improve the effect of the material discrimination.

A real-time mark algorithm module is incorporated within the data processing computer in the substance identification system, for performing real-time adjustment on the classification parameters so that they are favorable for the dual energy state of the accelerator, after that they are used by the material differentiation module in the substance identification system for material differentiation based on dual-energy transparency data obtained by the high-energy dual-energy system.

As shown in FIG. 6, according to an embodiment of the invention, the thickness of the real-time mark material block is uniform in the direction of the rays. The auxiliary detection module 65 obtains the classification parameters for this thickness.

Alpha data information for respective material blocks in the real-time mark device is recorded during a classification parameter training procedure by using a mark material with known material properties and a thickness, as reference information for real-time mark. The dual-energy state during the classification parameters training procedure is referred to as a standard state below.

Figure 8:
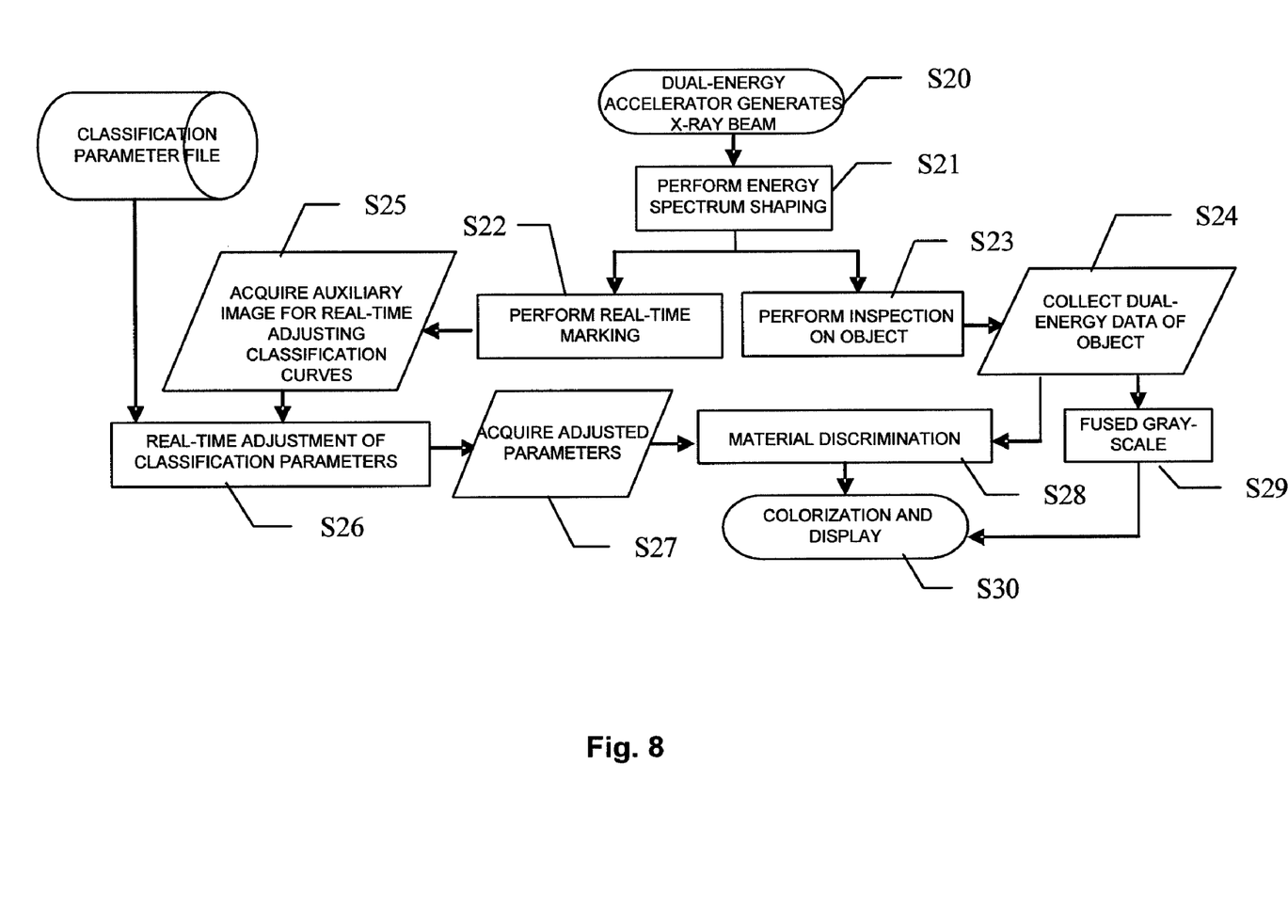
FIG. 8 is a schematic diagram of a procedure of real-time adjusting a classification parameter.

FIG. 8 is a schematic diagram of a procedure of real-time adjusting classification parameters. The procedure for real-time adjustment of the classification parameters will be described below.

At step S20, the ray generation unit 10 generates alternately dual-energy beams of rays, such as a first main beam of X-rays having a first energy and a second main beam of X-rays having a second energy. As described above, the ray generation unit 10 also generates a first auxiliary beam of X-rays having the first energy and a second auxiliary beam of X-rays having the second energy in synchronization with the first main beam of X-rays and the second main beam of X-rays. As another embodiment, the first auxiliary beam of X-rays and the second auxiliary beam of X-rays are part of the first main beam of X-rays and the second main beam of X-rays. At step S21, in order to improve material identification result, the energy spectrum shaping unit 40 performs shaping on the first main beam and the first auxiliary beam and/or the second main beam and the second auxiliary beam so as to enlarge a distance between the two energy spectra.

At step S22, the first auxiliary beam and the second auxiliary beam transmit the real-time mark material blocks 61~64. The auxiliary detection module 65 collects the auxiliary beams that have transmitted respective real-time mark material blocks. Auxiliary image data for classification curve real-time adjustment is acquired and transmitted to the data processing computer at step S25.

At step S23, the first main beam and the second main beam transmit the object 20 to be inspected. The data collection subsystem 30 collects the first main beam and the second main beam that have transmitted the article 20 to be inspected. Dual-energy data for the article to be inspected is acquired and transmitted to the data processing computer at step S24.

At step S26, the real-time adjustment for the classification parameters is performed in the data processing computer.

As described above, the n-th column of normal image is adjusted before it is identified by using the classification parameters. Firstly, dual-energy attenuation coefficients for respective materials in auxiliary images corresponding to the (n−m)-th column of normal image to the (n+m)-th column of normal image are statistically computed (m is determined based on requirement of the system). After that, corresponding alpha data is computed.

Subsequently, classification parameters usable for the n columns of normal images are performed real-time adjustment.

According to an embodiment of the invention, here the classification parameters are parameters for alpha curves for respective materials, the normal alpha curves being shown in FIG. 10C. There are two adjustment methods. An organic material is taken as an example to describe the adjustment procedure below.

A first adjustment method is as follows. Alpha data for the carbon material block is computed in real time by the real-time mark device as (alphax1, alphay1). In standard state, alpha data for carbon being derived from classification curves with the low-energy alpha value being alphax1 is (alphax1, alphay2). Therefore, the adjustment coefficient is coff_alpha=alphy1/alphay2, which is used to adjust alpha curve for the entire carbon block.

Figure 11:
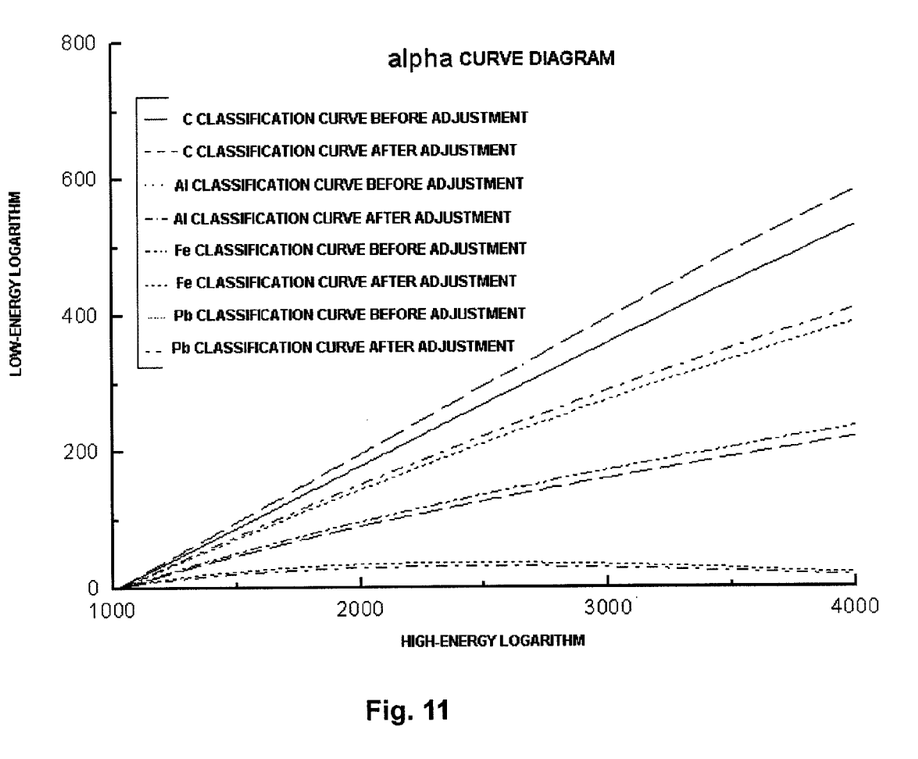
FIG. 11 is a chart showing the comparison result of alpha curves before and after adjustment.

A second adjustment method is as follows. The real-time mark device collects data at the time the auto mark unit conducts mark. At the time the classification curve is generated, average dual-energy attenuation coefficients for the carbon material block in the auxiliary images are statistically computed, and then corresponding alpha data (alphax2, alphay2) is computed and stored in advanced. When images are collected normally, alpha data for the carbon material block is computed in real time by the real-time mark device as (alphax1, alphay1). The adjustment coefficient is coff_alpha=(alphay1/alphax1)/(alphay2/alphax2), which is used to adjust alpha curve for the entire carbon block. Besides, if there are two carbon material blocks of two mass thicknesses, and the adjustment parameter for the block with lower mass thickness 1 is coff_alpha1, and that for the block with larger mass thickness 2 is coff_alpha2, then the adjustment principle is as follows. A value on the alpha curve corresponding to a mass thickness lower than the mass thickness 1 is adjusted with the coefficient coff_alpha1. A value on the alpha curve corresponding to a mass thickness larger than the mass thickness 2 is adjusted with the coefficient coff_alpha2. An adjustment coefficient for a value corresponding to a mass thickness larger than the mass thickness 1 and lower than the mass thickness 2 is obtained by linear interpolation of coff_alpha1 and coff_alpha2. In this way, the alpha curves for aluminum, iron and lead are adjusted respectively, to obtain adjusted classification parameters at step S27. Adjusted classification curves are shown in FIG. 11.

At step S28, material identification is performed on the n-th column of normal image by using adjusted new alpha curve. In order to accelerate identification speed, adjustment can be performed every some columns but not every column, depending on the requirement of the system.

Moreover, at step S29, the dual-energy images are subjected to gradation fusion at the time of material differentiation. At step S30, the result of material differentiation and that of gradation fusion are inputted into a colorization module, and are colorized therein. The colorized final material differentiation result is presented to a user.

Furthermore, according to another embodiment of the invention, the real-time mark material block may have two thicknesses. In this case, the classification parameter for a first thickness and that for a second thickness are adjusted respectively, rather than that the classification parameters for different thicknesses are adjusted with a single parameter. As a result, the accuracy for material identification is improved.

Also, for a system with large accelerator space, the real-time mark device according to an embodiment of the invention may be arranged below the sectorial beams of rays required by normal scanning. Output port of the accelerator is enlarged so that auxiliary beams are below main beams.

For a system with small accelerator space, the real-time mark device according to an embodiment of the invention may be arranged above the sectorial beams of rays required by normal scanning. Output port of the accelerator is enlarged so that auxiliary beams are above main beams. Optionally, an auxiliary output port is added at the output port of the accelerator, and the material block in the real-time mark device is arranged in regions covered by rays outputted from the auxiliary output port.

As another embodiment, the auxiliary beams of rays can be a part of the main beams that are rarely used, commonly are those at the top of the main beams. The real-time mark detector can be the detection module on the top of the arm of the scanning detector. In the case, the auxiliary detection module 65 is omissible. The data processing subsystem 30 transmits collected auxiliary image data and dual-energy data directly to the data processing computer.

When the main beams collect air data, the auxiliary beams also collect air data. The real-time mark material block should be removed off so as not to block auxiliary beams of rays when air data is collected.

In general, the real-time mark detection module should be arranged between the accelerator and the object to be inspected so that the distance to the target point of the accelerator is smaller than that from the scanning detection module in the data collection subsystem. If the same detection module is used, then saturation will be reached soon. Therefore, the auxiliary detection module in the invention has a dynamic range that is larger than that of the detection module in the data collection subsystem.

As said above, each column normal data is adjusted before it is identified by using classification parameters. A better identification result will be obtained at the cost of low operation speed.

According to another embodiment of the invention, classification parameter can be adjusted every some columns, such as every 4 column, to accelerate operation speed.

Figure 12:
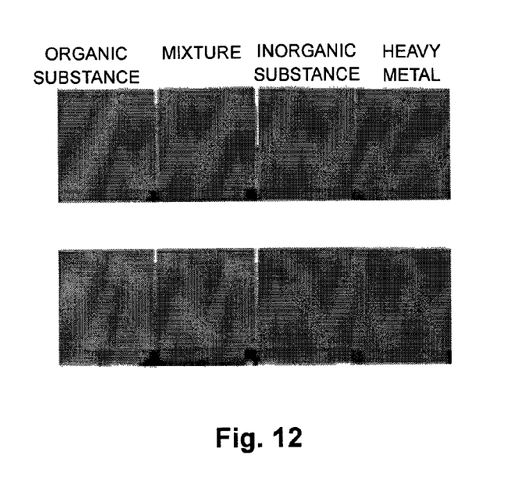
FIG. 12 is a schematic diagram shows the material identification results before and after adjustment of classification parameters when the accelerator state changes.

FIG. 12 shows the material identification results before and after adjustment of classification parameters when the accelerator dual-energy state changes. From the above part of FIG. 12, it can be seen an error result will be obtained if original classification parameter is used for material differentiation after the accelerator dual-energy state changes. With a mark system, the fluctuation of the accelerator dual-energy state will be adapted and a right material differentiation result can be obtained, as shown in lower part of FIG. 12. To sum up, the method and device according to an embodiment of the invention can improve the stability of the substance identification result.

Although exemplary embodiments of the present invention have been described hereinabove, it should be clear to those skilled in the field that any variations and/or modifications of the basic inventive concepts will still fall within the scope of the present invention, as defined in the appended claims.

What is claimed is:

1. A real-time mark method for a substance identification system which identifies a substance in an article to be inspected based on a set of classification parameters, the method comprising the steps of:
   simultaneously emitting a first main beam of rays and a first auxiliary beam of rays having a first energy, and simultaneously emitting a second main beam of rays and a second auxiliary beam of rays having a second energy;
   causing the first and second main beams of rays transmitting through the article to be inspected;
   causing the first and second auxiliary beams of rays transmitting through at least one real-time mark material block;
   collecting values of the first and second main beams of rays that have transmitted through the article to be inspected as dual-energy data;
   collecting values of the first and second auxiliary beams of rays that have transmitted through the real-time mark material block as adjustment parameters;
   adjusting the set of classification parameters based on the adjustment parameters; and
   identifying the substance according to the dual-energy data based on adjusted classification parameters.

2. The real-time mark method of claim 1, wherein adjusting the set of classification parameters based on the adjustment parameters is performed every predetermined time number of scanning.

3. The real-time mark method of claim 1, wherein the at least one real-time mark material block comprises a first block representing an organic substance, a second block representing a mixture, a third block representing an inorganic substance and a fourth block representing a heavy metal.

4. The real-time mark method of claim 3, wherein the first block is made of carbon, the second block is made of aluminum, the third block is made of iron and the fourth block is made of lead.

5. The real-time mark method of claim 1, further comprises a step of adjusting energy spectrum of respective beams of rays by an energy spectrum adjustment unit.

6. The real-time mark method of claim 1, wherein the first auxiliary beam of rays is part of the first main beam of rays, and the second auxiliary beam of rays is part of the second main beam of rays.

7. The real-time mark method of claim 1, wherein the first auxiliary beam of rays is separated from the first main beam of rays, and the second auxiliary beam of rays is separated from the second main beam of rays.

8. The real-time mark method of claim 6, wherein the at least one real-time mark material block is arranged in the upper portion, lower portion or side portion of the first or second main beam of rays.

9. The real-time mark method of claim 1, wherein the at least one real-time mark material block has a single thickness respectively.

10. The real-time mark method of claim 1, wherein the at least one real-time mark material block has at least two thicknesses respectively.

11. The real-time mark method of claim 1, wherein the classification parameters form a discretized classification curve that can differentiate at least two substances from each other.

12. A real-time mark device for a substance identification system which identifies a substance in an article to be inspected based on a set of classification parameters, the real-time mark device comprising:
   a ray generation unit for simultaneously emitting a first main beam of rays and a first auxiliary beam of rays having a first energy, and simultaneously emitting a second main beam of rays and a second auxiliary beam of rays having a second energy, the first and second main beams of rays transmitting through the article to be inspected, the first and second auxiliary beams of rays transmitting through the at least one real-time mark material block;
   a collection unit for collecting values of the first and second main beams of rays that transmit through the article to be inspected as dual-energy data, and collecting values of the first and second auxiliary beams of rays that transmit through the real-time mark material block as adjustment parameters;
   a data processing unit for adjusting the set of classification parameters based on the adjustment parameters, and identifying the substance according to the dual-energy data based on adjusted classification parameters.

13. The real-time mark device of claim 12, wherein the collection unit further comprises:
   a main detector module, whose detection surface is substantially perpendicular to a center line of the first or second main beam of rays, and for detecting the first or second main beam of rays that has transmitted through the article to be inspected;
   an auxiliary detector module, whose detection surface is substantially perpendicular to a center line of the first or second auxiliary beam of rays, and for detecting the first or second auxiliary beam of rays that has transmitted through the real-time mark material block.

14. The real-time mark device of claim 12, wherein the at least one real-time mark material block is arranged in the upper portion, lower portion or side portion of the first or second main beam of rays.

15. The real-time mark device of claim 12, wherein the data processing unit adjusts the set of classification parameters based on the adjustment parameters every predetermined time number of scanning.

16. The real-time mark device of claim 12, wherein the at least one real-time mark material block comprises a first block representing an organic substance, a second block representing a mixture, a third block representing an inorganic substance and a fourth block representing a heavy metal.

17. The real-time mark device of claim 16, wherein the first block is made of carbon, the second block is made of aluminum, the third block is made of iron and the fourth block is made of lead.

18. The real-time mark device of claim 12, wherein the first auxiliary beam of rays is part of the first main beam of rays, and the second auxiliary beam of rays is part of the second main beam of rays.

19. The real-time mark device of claim 12, wherein the first auxiliary beam of rays is separated from the first main beam of rays, and the second auxiliary beam of rays is separated from the second main beam of rays.

20. The real-time mark device of claim 12, wherein energy spectrum of respective beams of rays are adjusted by an energy spectrum adjustment unit.

21. The real-time mark device of claim 12, wherein the at least one real-time mark material block has a single thickness respectively.

22. The real-time mark device of claim 12, wherein the at least one real-time mark material block has at least two thicknesses respectively.

23. The real-time mark device of claim 13, wherein the auxiliary detection module has a dynamic range that is larger than that of the main detection module.

* * * * *